United States Patent
Lofgren et al.

(10) Patent No.: US 11,395,755 B2
(45) Date of Patent: Jul. 26, 2022

(54) METHOD FOR APPLYING SPINAL TRACTION

(71) Applicants: Michael Shane Lofgren, Tualatin, OR (US); Brian Charles Stewart, Oregon City, OR (US); Sean Jeremiah Harrington, Los Angeles, CA (US)

(72) Inventors: Michael Shane Lofgren, Tualatin, OR (US); Brian Charles Stewart, Oregon City, OR (US); Sean Jeremiah Harrington, Los Angeles, CA (US)

(73) Assignee: BAXRELAX LLC, Tualatin, OR (US)

( * ) Notice: Subject to any disclaimer, the term of this patent is extended or adjusted under 35 U.S.C. 154(b) by 361 days.

(21) Appl. No.: 16/351,472

(22) Filed: Mar. 12, 2019

(65) Prior Publication Data
US 2019/0365558 A1    Dec. 5, 2019

Related U.S. Application Data

(62) Division of application No. 14/089,138, filed on Nov. 25, 2013, now Pat. No. 10,278,856.

(51) Int. Cl.
*A61F 5/04* (2006.01)

(52) U.S. Cl.
CPC ..................... *A61F 5/04* (2013.01)

(58) Field of Classification Search
CPC .. A61F 5/04; A61F 5/042; A61F 5/048; A61F 5/05808; A61F 5/05816; A61F 5/05833
See application file for complete search history.

(56) References Cited

U.S. PATENT DOCUMENTS 9,427,371 B1 * 8/2016 Lamar ................. A47C 1/032
2006/0224097 A1 * 10/2006 Bass ................... A61H 1/0296
602/32

* cited by examiner

*Primary Examiner* — Tarla R Patel

(57) ABSTRACT

A method is provided for treating back pain whereby a person sits comfortably in a seated position in a chair and fastens their upper body above the waist to the seat back and fastens their lower body at just above the buttocks and then by means of leaning back allows the seat back to pull the person's upper body away from their lower body providing spinal traction.

17 Claims, 14 Drawing Sheets

METHOD FOR APPLYING SPINAL TRACTION

BACKGROUND OF THE INVENTION

Field of the Invention

It has long been known that back pain is a common and persistent problem for a very large number of people. It is one of the most common reasons to visit a doctor, among the most common reasons to miss work and very debilitating to anyone suffering from this condition. For many years doctors, inventors, chiropractors, fitness instructors, yoga practitioners and others have sought to find a way to minimize back pain to any degree and for any length of time. There is no known cure for back pain but a regimen of exercise, muscle stabilization techniques, yoga or stretching and rest seem to be the most effective regimen to treat chronic back pain. Surgery can be an option for back pain related to trauma but is not always effective for non-traumatic back pain; which is the most common type.

Faced with chronic back pain, may individuals begin some type of traction therapy. Traction therapy has its believers and doubters but it is generally accepted that traction therapy although not a cure for back pain is often helpful in minimizing daily back discomfort and when used on a regular basis helps control the recurrence of lower back tightness, pain and discomfort. Present traction options are often times expensive if administered in a doctor's or chiropractor's office and home traction devices are often times ineffective because of equipment short comings or are difficult to operate and hazardous to use.

What the present invention provides is a device that will be easy to use, easy to engage, safe, effective and affordable. The problems with existing traction devices are that they are difficult for many people to use, especially when experiencing the tightness, pain and lack of mobility that accompanies back pain. One of the most prevalent back traction devices is the inversion table and it is sold worldwide in the millions of units. This machine can be very difficult to use on a sustained basis and has been associated with falling, glaucoma, extreme blood flow to the head and other debilitating and undesirable conditions and situations. Nevertheless, in desperation, many individuals purchase inversion tables with the hope of relief from back pain. The traction aspect works for many people; the inversion does not. Other devices are table type traction devices that can be set up on the floor or on a bed and have straps that wrap around the patent's hips and torso. A pneumatic cylinder actuated by a pump driven by the patient's hands spreads the two halves of the table and attempts to apply traction to the patient. The concept would appear to be a good approach but the belts are unable to effectively grasp the patient's body because of the inadequate strap design and routing resulting in the strap's inability to hold the body against a mostly flat surface and therefore the strap either slips relative to the body or the patient's clothing moves but the spinal column does not elongate and so little decompression of the spine takes place. This type of traction is also difficult to get in and out of since it requires the user to get down on their knees when using the device on the floor or crawl around on hands and knees when attempting to use this type of machine on a bed or elevated surface.

What is needed is a device that is easy to get into, comfortable to use, not dangerous and most important, effective. The present invention addresses and solves all of these problems very effectively. The present invention is as easy to engage as sitting in a chair. It is as safe as laying in a lawn chair and is very effective at applying traction and effective decompression of the lower spine. The essence of the invention is the unique ability of permitting the patient to sit in a chair like device, apply a torso engaging strap that is specifically designed and shaped to effectively grab the patient's torso. When seated a uniquely designed lower strap is configured to wrap around the rear of the buttocks in the sacral areal of the lower back, around the sides of the hips and over the thighs to an anchor post in between the patient's legs. When the patient leans back, the upper and lower body strap move away from each other and decompression is applied to the patient's lower spine. The action of moving from a seated position to a supine position with a strap that effectively grabs the patient's buttocks, hips and lower body and a strap that grabs the upper body and pulls the patient's upper body away from the lower body as the patient leans back is the essence of the present invention. It is very effective, very comfortable and very easy to administer.

No other traction device is able to provide this safety, effectiveness and ease of access. Regardless of age or physical impairment, the present invention will provide some amount of relief for sufferers of back discomfort to the extent that traction is able to provide therapy.

DESCRIPTION OF THE RELATED ART

There are many types of methods and apparatus that involve some type of stretching of the spine generally in the lumbar region of the lower back. These methods do not cure back pain but they have proven to be effective in some cases to minimize and control back pain. There are many devices that position or manipulate the body to result in spinal elongation. An inversion table is among the most common. In this device the patient, while standing, positions themselves against a table which is mounted such that it can pivot and place the patient at various angles of inversion. The patient locks his or her ankles into the inversion table and then, after adjusting for their height, leans back and begins to hang inverted, upside down, so that gravity acting on the weight of the body causes the spinal column and essentially the entire body from the ankles downward to stretch depending on the angle of inversion. This is said to be effective and has shown positive results in some patients but is sometimes difficult to use and is contra-indicated for people with glaucoma or high blood pressure. The amount of time a person can be in this position is limited and varies from person to person. Some elderly or infirm individuals may find it difficult or uncomfortable to use and to be in what is to many an awkward position.

Other devices seek to apply traction by positioning the patient in a seated position with legs bent and feet hooked under constraints to keep the body in place. Then the entire chair is inverted and the person hangs upside down like the standing inversion tables. But in this case it is mostly the upper body that is subjected to the stretching caused by the weight of the body and gravity. Again, with this procedure it is uncomfortable for some and cannot be used by individuals with certain health conditions as mentioned above.

Traction can be applied in many ways; hanging upside down, partially upside down, laying in a supine or prone position while having the upper and lower parts of the body pulled in opposite directions, bending over an object either in a supine or prone position or leaning over an object in a kneeling position. Also, yoga and many stretching exercises and manipulation by a masseuse, doctor, therapist or chiropractor are used to initiate decompression of the spine. In this instance we will use traction to mean any means of gently, through the use of a device, elongating the spinal column for the purpose of minimizing pain or relaxing muscles or inducing a relaxed state of the body in order to minimize the pain associated with muscle spasms or back discomfort.

SUMMARY OF THE INVENTION

The present invention is directed at therapy for individuals suffering from lower back discomfort. There are an estimated 80% of the population with some form of lower back discomfort worldwide. 30% of Americans at any given time will experience some type of lower back discomfort. Lower back pain is second only to the common cold as a reason to visit a doctor. Surgery is only appropriate for approximately 5% of those who experience chronic back pain. Lower back pain is a very large problem worldwide and continues to be a problem. Back pain costs $50 billion dollars annually in the U.S.

The incentive is strong to find a means to minimize the discomfort of back pain for literally millions of people and many years and many methods have been tried some with varying amounts of success. The present invention addresses the problem of back pain by what is referred to as traction therapy.

Traction has been around for a long time and there are many machines and devices that hope to apply traction to individuals with back pain. Many of these processes and devices are complicated or expensive and some are contra-indicated for individuals with other medical issues along with their back pain. Many of the devices available are difficult to apply to individuals because of their structure.

The second type of traction device, the table, is easier use than the inversion table and is commonly used in therapist's offices and chiropractor's and doctor's offices. Because sessions in doctor's offices are expensive, a market for home use traction devices has been around for several years and is growing. Typical home use devices are scaled down traction tables that are operated by pneumatic cylinders, are usually used on the floor or on the bed, are portable and have two flat surfaces with belts that respectively wrap around the person's torso and hips and when the two flat surfaces move away from each other under the force of the pneumatic cylinder, traction is applied the person's spine.

The problem with this type of device is the table is still difficult to get on to, it is difficult to securely grab the person with the straps when the platform surface is essentially flat, and the straps slide up the person's torso and down the hips before grabbing the body so the device moves apart but little decompression of the spine takes place. Also, the person using a pneumatic device like this has to pump the pump while laying on their backs on the table; a difficult task in itself. The more common experience when using the portable pneumatic device is the removal of the person's pants because the person lying flat on a flat surface with a belt wrapped around the hips does not provide an adequate body part, when in this position, for the lower strap to grab.

There are other types of traction devices. Some are worn around the waist and buttocks with expansion means such as pneumatic cylinders or mechanical jacking mechanisms to push the two respective halves apart and can be worn while standing. Some devices are like a gently humped curved surface which the person lies upon face-up with the humped surface in the middle of their back causing their back to be stretched over the curved surface.

The present invention is directed toward providing a means for applying traction or what has become referred to as spinal decompression that is effective, easy to apply and within a range of expense that will let the device be suitable for either in home use or clinical use. The present invention addresses all the problems presented by the above mentioned traction devices. The present invention does not invert the user so it eliminates any contra-indicated medical conditions that would prevent persons from using it. The present invention allows the user to simply sit down on the seat and attach the hip and buttock's strap to secure the lower body and the torso strap wrapped under the rib cage to secure the upper body. The present invention does not require pneumatic or hydraulic pressure to apply the traction although both could be a part of various embodiments of the present invention. The preferred embodiment of the present device relies on the user's body position in conjunction with the design of the device to apply an adjustable and progressive amount of traction to the user's spine. The spectrum of presently available traction devices ranges from ineffective to uncomfortable, from expensive to unpleasant and still the need persists for an effective, affordable spinal traction device.

The present invention addresses and remedies all of these problems. The present invention is easy to use, inexpensive, uncomplicated and effective at applying spinal traction.

Operation of the Device

To use the invention in its preferred embodiment the individual sits on the seat with feet on the ground. Then he or she reaches down to each side of their thighs and removes the lower body strap loops from the loop securing posts at the outside of each thigh. After removing the strap loops from their brackets, the individual would place each strap over each thigh and connect the loops to the securing anchor points between the knees at the front edge of the seat by placing the elastic loops over the anchor points. This aspect of the present invention is very important in the operation of the back traction device. The straps come around from behind the individual's buttocks at the base of the spine and extend over the individual's thighs and towards the front of the knees where they are secured at the anchor points at the front edge of the seat between the individual's knees. This strap configuration grabs onto the individual's lower body, hips and buttocks and is one of the key components in the effective use of the back traction device. The strap grabs the user and pulls on the lower body in such a manner as to restore the anatomically correct arch in the user's lower spine. Elastomers may be added to the end of the strap and secured to the anchor points. These stretchable elastomers allow the device to be tuned to the amount of spinal stretch desired as the user leans back. Although not a requirement for the safe operation of the invention, the elastomers may also help protect the user from injury by removing the shock of reclining too quickly or too far. Varying strength elastomers may be suggested for different body weight individuals or individuals that want more or less decompression applied to their spine relative to the amount of recline of the device.

Now the individual will reach down and slightly behind their back at each side and grasp the torso strap. Then, take the torso strap and wrap it around their waist just below the ribcage and connect the strap together by overlapping the male and female Velcro portions of the strap. Many types of straps and securing devices may be used. In this embodiment, Velcro is used but any means of connecting the straps together that provides some type of adjustment that allows for snugging of the strap against the body would work. As the individual reclines the upper body is moved away from the seat towards the rear. The elastomers stretch and while stretched attempt to pull the lower body back towards the front of the seat. The elastomers may be of differing strengths further allowing the adjustment of the amount of traction applied during the use of the device.

The preferred embodiment may include a heated pad at the base of the spine to add comfort and relax the muscles at the initiation of traction.

Now the individual is ready to begin the traction procedure. The individual will reach down with his heal while sitting upright and release the locking mechanism that will then permit the seat back to recline. Once the locking mechanism has been released the individual will begin to lean back against the seat back while gently unweighting the legs and feet. This will cause the user to recline and the legs to raise upward. Gently raising the legs will allow for the individual to gradually recline towards a supine position. The more the individual lifts or un-weights the legs the further back the upper body will recline.

As the upper body reclines, because the strap engaging the upper body torso area is fixed to the seat back at a location removed from the pivot point between the seat back and the seat and because the buttocks and lower body are engaged by the lower strap and constrained by the anchor point forward of the seat and between the operator's legs, as the operator reclines to a supine position the upper body strap moves a distance away from the front anchor point which is securing the operator's lower body and buttocks and therefore exerting a pulling motion on the operator's upper body relative to the buttocks and lower body causing a gentle decompression of the spinal column at the base of the spine. The greater the recline, the greater movement of the torso strap relative to the lower body and buttocks strap resulting in elongation of the flexible elastomers anchored to the front anchor point. The stretched elastomers exert a continuous force on the operator's lower body and buttocks pulling the lower body away from the upper body which is constrained and held in place by the upper body strap resulting in a gentle and pleasing stretching of the lower back and traction effect applied to the lower back and spinal cord. There are several possible location points for the upper body torso strap away from the pivot point. Adjustable straps are attached to the torso strap to raise or lower the torso strap toward or away from the pivot point between the seat and seat back allowing for adjustment for different sized individuals.

The action of reclining the seat back relative to the seat while the user is constrained respectively to the seat back by the torso strap and the front anchor points by the lower strap initiates the decompression of the spine. Gravity naturally encourages the operator to recline once the latch mechanism is released and the operator begins to allow his or her body to recline. In the preferred embodiment, the connecting linkage between the seat back and foot support is adjustable in order to balance the operator's upper and lower body weight distribution so that the operator may gently recline and gently stretch the lower spine.

The individual will continue to lean back until he or she is in a supine position. At this position maximum traction is applied to the lower back and spine. The individual may reach his hands back over his head to attain maximum recline of the backrest.

There are many ways to initiate traction or the decompression of the spinal column as the user reclines from a seated position to a supine position. In the preferred embodiment the user's spine is stretched by degree depending on the amount of recline, the location of the upper body strap and the strength of the elastomers. Separation of the lower body and upper body could also be accomplished by various rods, linkages, ropes and sheave mechanisms that would engage the upper or lower strap, pull one or both away from the other and initiate decompression as the user reclines from the seated to the supine position. For example, the lower body strap could be connected by cable from the strap, over a pulley located between the operator's knees and downward towards the floor to a an anchor point, weight, spring or some other means of resisting or applying pressure to the cable and thereby stretching the operator's lower back and spine as the operator reclines. The upper body strap could be pulled upon in a similar manner by attaching a cable to the upper body strap and running it toward the rear of the device over a sheave and anchored to an anchor point, elastomer or some other means to apply tension to the cable as the user reclines, pulling the upper body strap away from the lower body strap and thereby applying stretching, traction or decompression to the operator's lower back and spinal column. The present invention is intended to include any and all linkages, cables, ropes, sheaves and devices that initiate decompression of the spinal column as the user's upper body and lower body are stretched by confining straps as the user reclines from a seated to a supine position.

In the preferred embodiment and for the comfort of the user a leg support is provided that raises the user's legs as the user reclines. The device, for the purpose of traction of the back, would work equally as well without the leg support. The user while seated could secure the lower strap at the anchor point, the upper strap under the ribcage and lean back to initiate the desired amount of traction. Or, in the same position and configuration of the device but with the addition of mechanical controls such as a hydraulic cylinder and control station, attach upper and lower straps and initiate traction of the spine as the user reclined from a seated to a supine position.

Depending on the desired amount of time the operator desires to be in traction or stretching of the lower back and spine, the individual may terminate the stretching action of the device by reaching down with each hand to the handles at each side of the seat and while gently weighting the legs and bending the head and body forward, gradually return to an upright seated position.

To increase the amount of traction the individual may desire to increase the tension in the lower strap by taking up the slack in the strap. Now as the individual leans back in a similar manner as the initial effort the amount of resistance of the elastic loops or elastomers will be greater, the reclining motion will be resisted to a slightly greater degree and the amount of decompression of the spine will be increased. The individual may repeat this process several times to achieve the perfect amount of spinal stretch. This can be at the direction of the doctor or chiropractor or can be to a specified stretch of the elastic bands. Elastic bands of different elasticity may be used to provide more or less resistance.

During this process the individual will spend some amount of time in the applied traction position. The time in traction can vary and will depend on the individual. The individual may spend several minutes all the way reclined in a supine position or the individual may go through a series of reclines and upright maneuvers, whichever may be preferable, for some types of therapy especially under the direction of a doctor or chiropractor or physical therapist.

When the applied traction is to be terminated, the individual will put his or her hands on the handles at each side of the seat and pull their body upward while applying gentle weight to the legs and leaning the head and body forward to return to an upright position. In the upright position the locking mechanism will secure the leg support and backrest in a locked position. The individual will remove the torso constraint and drop it down to the side and then release the lower body strap at the anchor points between the knees and place the elastic loops at the docking stations at each side of the thighs. Finally, the user will rotate the lower body strap anchor point forward, down and out of the way to enable easy departure from the invention.

The individual is now free to stand up and feel the relaxed feeling throughout the lower back and experience a relief from lower back discomfort.

While the preferred embodiment of the present invention as presented above relies on the individual to initiate reclining of the seat back relative to the seat, the device would work equally as well with a hydraulic cylinder, pneumatic cylinder or linear actuator to recline the seat back and or raise the leg support if a leg support is provided. Control means to limit, position or extend the amount of recline may be provided. In this embodiment of the present invention traction could be administered under the supervision of a doctor, chiropractor or therapist. The patient's involvement would be passive regarding the amount of recline and stretch and would permit medical or professional personnel to administer the procedure. In this embodiment the linear actuator, hydraulic cylinder or pneumatic cylinder may be attached to the linkage arm or to the leg support or seat back and when extended or retracted would initiate the reclining of the seat back relative to the seat and initiate traction.

There is elastic material between the torso strap and the lower body strap. This elastic material keeps the lower body strap in the correct position to wrap around the user's buttocks, hips and thighs but is able to stretch as the lower body strap moves away from the torso strap as the user reclines the seat back.

In the preferred embodiment the seat back support tube is separated into two sections to facilitate packaging. Because the seat back support tube connection is separated into two pieces a locating rotational stop screw is located in the upper section of the two piece seat back tube. The purpose of this screw is for proper rotational alignment of the two sections of tube so that the seat back pans are in essentially the same plane and to resist rotation of one section of the seat back tube relative to the other.

Both the upper and lower straps are adjustable both in their ability to secure the upper and lower parts of the user's body and also adjustable relative to the seat bottom and seat back to accommodate different size users.

The lower strap anchor point rotates forward and downward to move out of the way when the user gets on and off the device. This is an important factor in the ease of use of the back traction device. It may be found to be more comfortable to have the lower strap extend forward horizontally after coming over the thighs and forwardly to the anchor point between the user's legs. At the same time it is convenient to be able to move the anchor point downward and out of the way to facilitate getting on and off of the seat without bumping into the anchor point.

In the preferred embodiment the seat bottom cushion and seat back cushions are padded. It may be preferable to make the seat bottom and seat back out of webbing stretched over a tubular frame. The use of pads and seat back and bottom pans are not intended to limit the many ways the user may be able to be comfortably seated.

In the preferred embodiment the seat back cushions and corresponding seat back pans are adjustable up and down relative to the seat back tube for optimum comfort.

DETAILED DESCRIPTION OF THE PREFERRED EMBODIMENT

Many materials would be well suited for the manufacturer of the present invention and many processes for manufacturing would be possible to make the present invention. The following description of the invention is one of many possible embodiments of the present invention and is put forth as a preferred embodiment but not as by limitation to a particular material or process of manufacturer.

It will be appreciated that the following description of the invention is not in a particular order or sequence but one possible combination of parts which will enable the structure of the invention to be produced.

Figure 5:
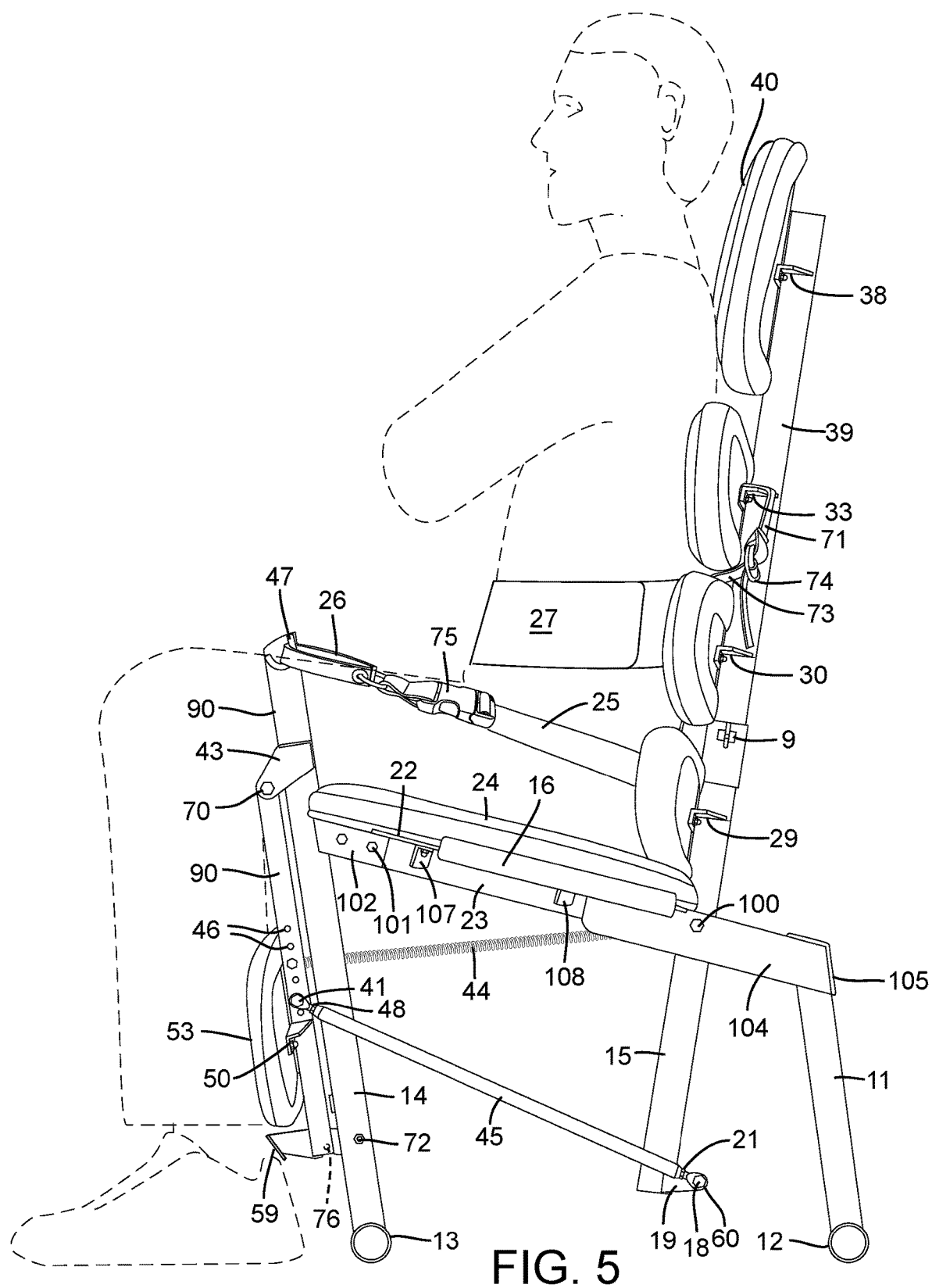
FIG. 5 is a left side view of the present invention in the upright position with an individual shown in dotted lines.
Figure 12:
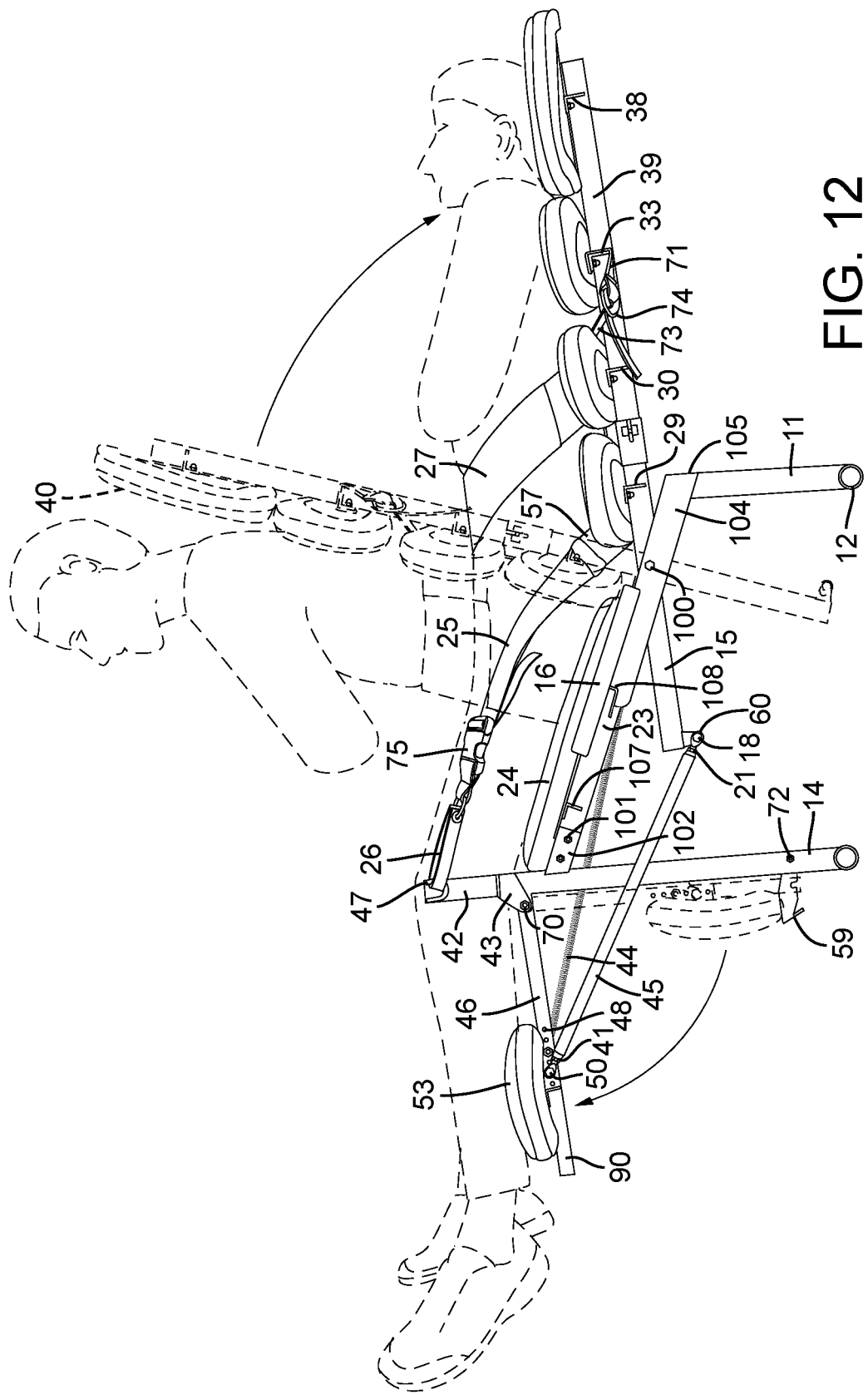
FIG. 12 shows the ability of the present invention to recline from the seated position to the supine or reclined position with the operator dotted in for reference.

FIG. 12 shows the individual in both the seated and reclined position and will be referred to for the purpose of explaining in detail the operation of the present invention. When the operator is seated, the lower strap 25 is wrapped around the sacral area of the operator's lower back then wraps around the hips, extends over the thighs and connects to the front anchor point 47 between the operator's legs in front of the seat 24. At this time the adjustable strap 25 may be slightly tightened putting minimal tension in the elastomer loops 26 at the end of the strap 25 on both sides where these loops attach to their respective anchor points 47. In FIG. 5, it will be noted that the operator's head is above the top back support pad 40 in this position and the torso strap 27 is horizontal and essentially perpendicular to the operator's body at the waist and secured around the waist, in the preferred embodiment, just below the ribcage. In this position the operator's legs would be bent at the knees and the feet on or near the floor. As the operator reclines the upper body strap 27, because it is attached to the seat back moves away from the anchor point 47 at the front of the seat 24 pulling the operator's body along with it as it reclines; the greater the recline the greater the distance the upper body is pulled. Simultaneously, the lower body, buttocks and hips is pulled along with the upper body along the seat and away from the anchor point 47. As this happens, the lower strap 25, which is wrapped around the hips and sacral area also attempts to follow the body and in so doing stretches the elastomer loops 26 at the ends of the lower body strap 25. As the elastomer loops 26 stretch, they try to return to their un-stretched position and in so doing exert a pulling motion on the lower body at the buttocks and hips. While this is happening the torso strap 27 engages the upper body just below the ribcage and begins to pull on the upper body and at the same time move the upper body away from the hips and buttocks. The combination of the torso strap 27 pulling the upper body up and away from the front anchor point 47 and the elastomer loops 26 at the ends of the lower body strap 25 pulling the lower body, buttocks and hips back to the front anchor point 47 puts the body in what is referred to as traction. Although significant movement occurs in the elastomer loops 26, the seat back 39 relative to the seat 24, the torso strap 27 relative to the lower strap 25, only a few millimeters of movement occurs in the spinal column. This movement provides decompression of the spinal column or traction of the spine. The present invention provides a very economical and effective device for providing traction and spinal decompression for the millions of people afflicted with non-surgically treatable back pain.

In FIG. 5 tube 14 is attached to base support tube 13. Many processes would permit this to be accomplished but in the preferred embodiment tube 14 is welded to base support tube 13. Similarly tube 11 is welded to base support tube 12.

Plate 102, FIG. 5 is welded to the top of tube 14. Plate 111, identical to 102 and not shown is welded similarly to top of tube 14 opposite plate 102. Cap screws and nuts 101 attach plates 102 and 111 to forward end of tube 23. In FIG. 5, the opposite or rearward end of tube 23 is attached to plate 104 and plate 106 not shown by welding. In FIG. 5, plate 105 is welded to ends of plates 104 and 106 respectively forming a boxed end of plates 104, 106 not shown and 105 respectively. Rear tube support 11 is inserted in between plate 104 and corresponding plate 106 not shown on the opposite side and is locked into place by cap screw 120 FIG. 4. In FIG. 5, the combination of tubes 11, 12, 13, 14 and 23 and plates 111, 102, 104, 106 and 105 along with cap screws and nuts 101 and 120 make up the main support structure for the preferred embodiment of the present invention. It will be appreciated that this is one means of providing support for the invention but there could be many different combinations to attain the same result and nothing presented herein is to be seen as by limitation.

Figure 3:
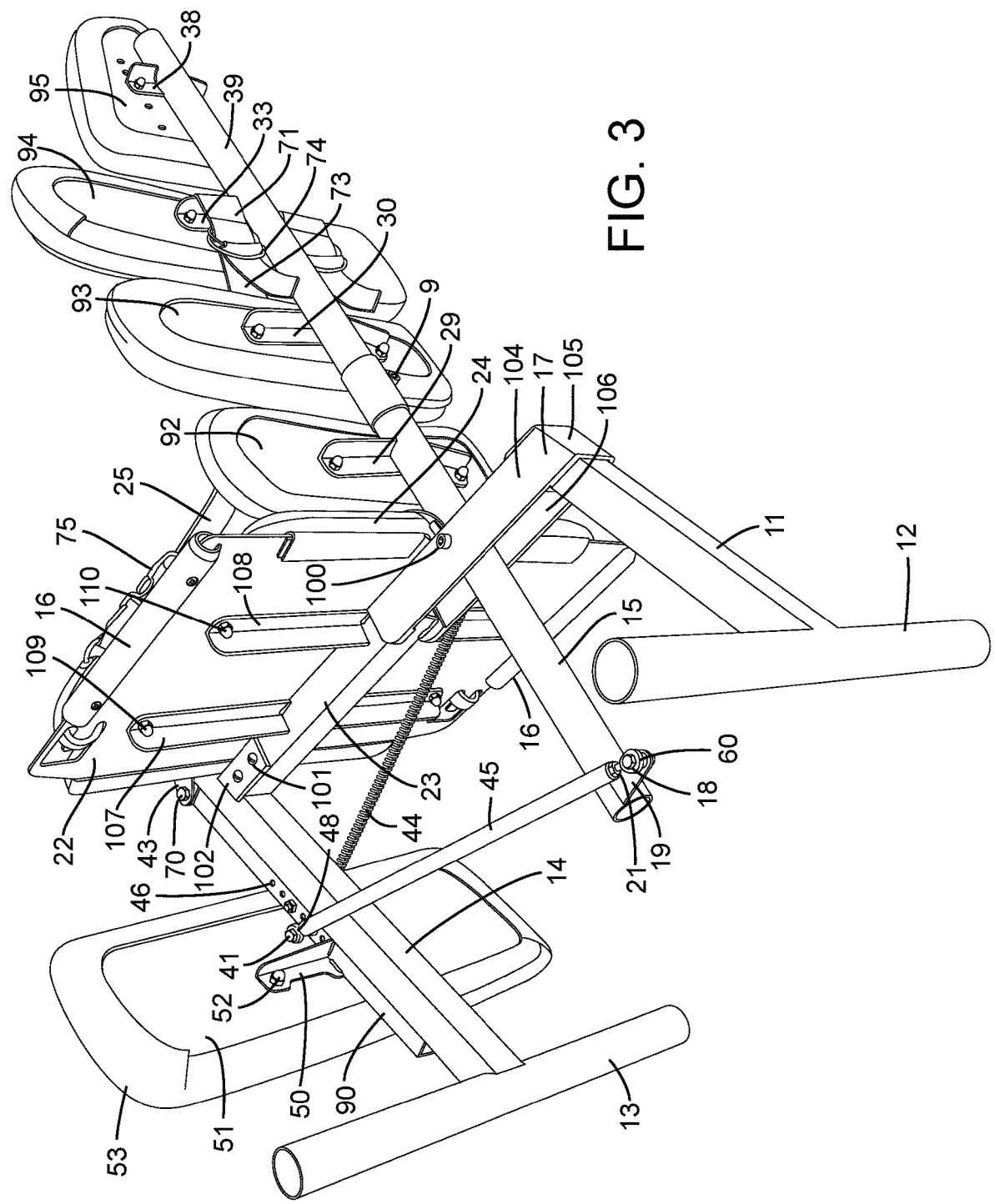
FIG. 3 is a pictorial view of the present invention in the upright seated position from behind and beneath.

In FIG. 5, bracket 107 is welded to tube 23 and likewise bracket 108 is welded to tube 23. Seat pan 22 rests on top of brackets 107 and 108 and is secured by pairs of cap screw and nut combinations 109 and 110, FIG. 3. Pad 24 is attached to seat pan 22. Seat pan 22 along with pad 24 are configured to seat the individual and would be just one of many means appropriate to support a person while seated on the present invention. In place of seat pan 22 and pad 24, webbing could be stretched around a tubing framework to provide a seating area for the individual or an injection molded or blow-molded plastic shape would be adequate to provide seating for the individual while using the invention. In FIG. 3, a pair of handles 16 is attached on each side of seat pan 22 to be gripped by the individual's hands when returning to an upright position.

In FIG. 3, tube 15 is pivotally connected to plate 104 and 106 by through shoulder bolt 100. In FIG. 3, Plate 19 is welded to bottom of tube 15. In FIG. 3, bolt 18 and spacer 60 (not shown) pivotally secure rod end 21 to plate 19.

In FIG. 3, tube 39 is journaled to slide into the end of tube 15 and is held in place by pinch bolt 9. A slot is machined into the end of tube 15 to receive alignment pin (not shown) for the purpose of restricting rotation of tube 39 relative to tube 15. In FIG. 3, four pairs of brackets 29, 30, 33 and 38 are welded one to each side, symmetrically to tube 39 for the purpose of attaching backrests. The back rests 92, 93, 94 and 95 are attached by cap screw and nut to brackets 29, 30, 33 and 38 respectively.

Figure 10:
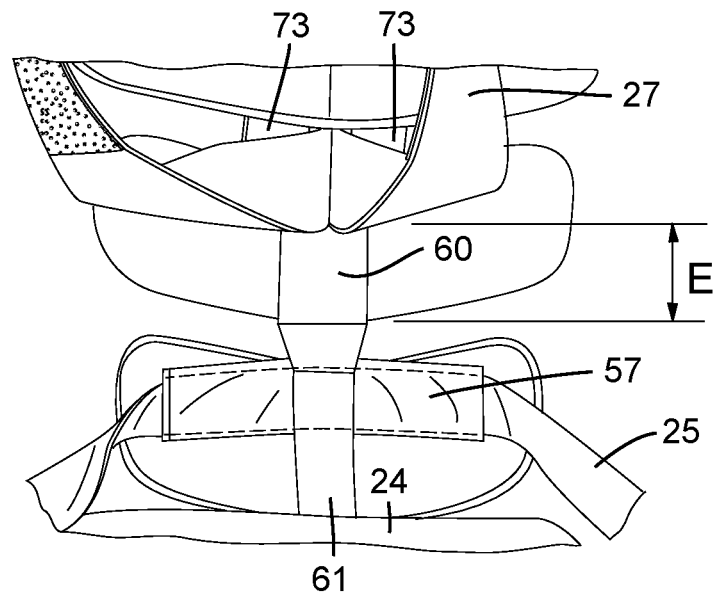
FIG. 10 shows elastic material between the upper body strap and the lower body strap in the relaxed position.
Figure 11:
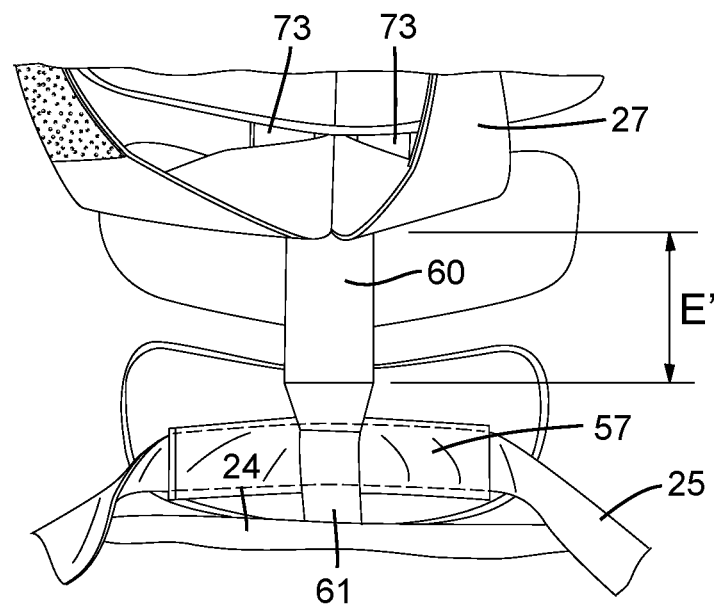
FIG. 11 shows the ability of elastic material between the upper body strap and the lower body strap to stretch as the upper body strap is moved away from the lower body strap.
Figure 13:
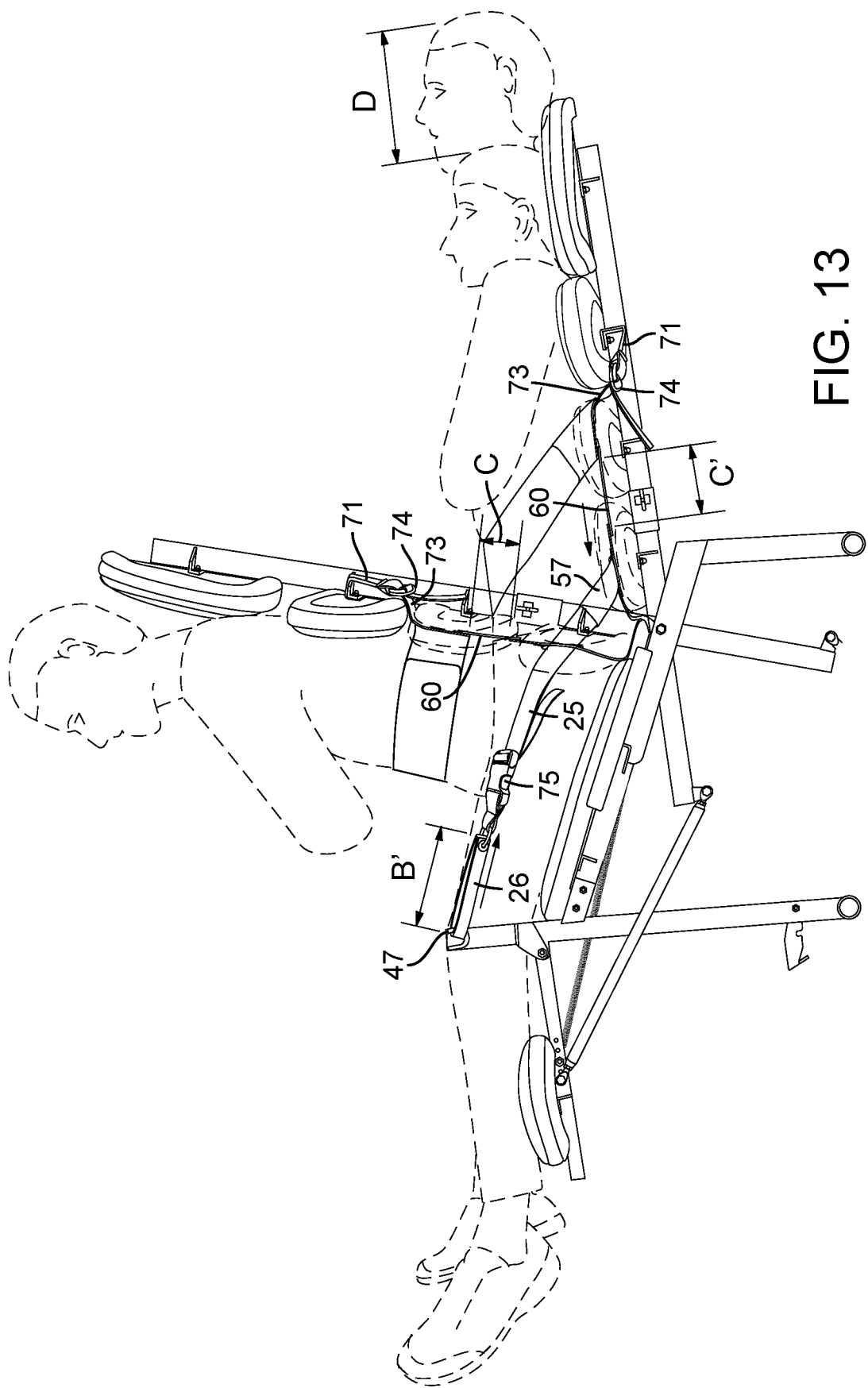
FIG. 13 shows the various movements of the straps, elastomers and the operator as the invention reclines from the upright seated to the reclined supine position. The operator's body position can be seen to shift relative to the seat back as the invention reclines.

In FIG. 3, backrest support tube 39 and lower tube 15 extend downwardly and are pivotally connected to plates 104 and 106 by means of pivot bolt 100. In FIG. 12, as tubes 15 and 39 along with back rest supports and upper torso strap 27 rotate reward about pivot bolt 100, torso strap 27 moves a distance away from anchor point 47. Correspondingly lower strap 25 moves away from anchor point 47 causing loops 26 to increase in length as shown in FIG. 13, dimension "B'". During the operation of the preferred embodiment of the present invention, the user's upper body is grasped generally just under the rib cage by torso strap 27. When the user leans back, and the upper body is grasped by torso strap 27, which in turn is secured to tube 39 at approximately seat back rest and pad support bracket 33, the distance as indicated by dimension "B'" increases relative to anchor point 47. In FIG. 5, the user's lower body and pelvic area is grasped by lower strap 25 which wraps around the user's body from the sacral area in the rear around the hips on each side and over the thighs towards the front anchor points 47. In FIGS. 10 and 11, strap 25 is able to slide through enclosed material 57, which holds lower strap 25 in position relative to elastic material 60 which holds lower strap 25 in position around the hips and buttocks. Lower strap 25 is in turn secured to anchor point 47 by means of stretchable connections 26 on each end of strap 25. Because the distance "B" increases as the user leans back and because the user's upper and lower body is grasped respectively by lower strap 25 and upper strap 27, the user's upper and lower body are gently pulled away from each other as strap 27 moves away from strap 25. The actual elongation of the user's spinal column is mere millimeters but the decompression of the vertebrae within the spinal column requires only a subtle movement to possibly provide temporary relief from the discomfort of back pain.

It will be appreciated that this movement of the torso away from the hips and lower body of the individual is what is generally referred to in the fields of medicine and physical therapy as traction or more recently as decompression. Generally a small elongation of the spine over a short period of time will result in a feeling of comfort and a feeling of the release of muscle tension or spasming. A gentle stretching of the lower back is effected by the constraint of the torso strap 27 securely fastened about the individual's lower torso just below the rib cage and the hip and lower body constraint 25 wrapped around the individual's buttocks and hips from the sacral area in the rear of the back, forwardly around the hips and over the thighs to the anchor points 47 in front of and between the user's legs as the individual leans back and the upper strap 27 moves away from the lower strap 25.

Pads are attached to back rests pans 92, 93, 94 and 95 which are in turn attached to brackets 29, 30, 33 and 38 respectively to provide padding for and engagement of the individual's back.

Figure 7:
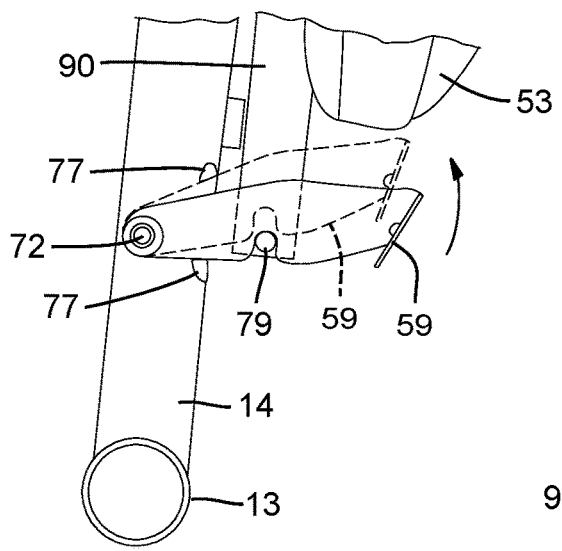
FIG. 7 is a view of the locking mechanism for the leg support shown in the locked position or dotted in the unlocked position.
Figure 8:
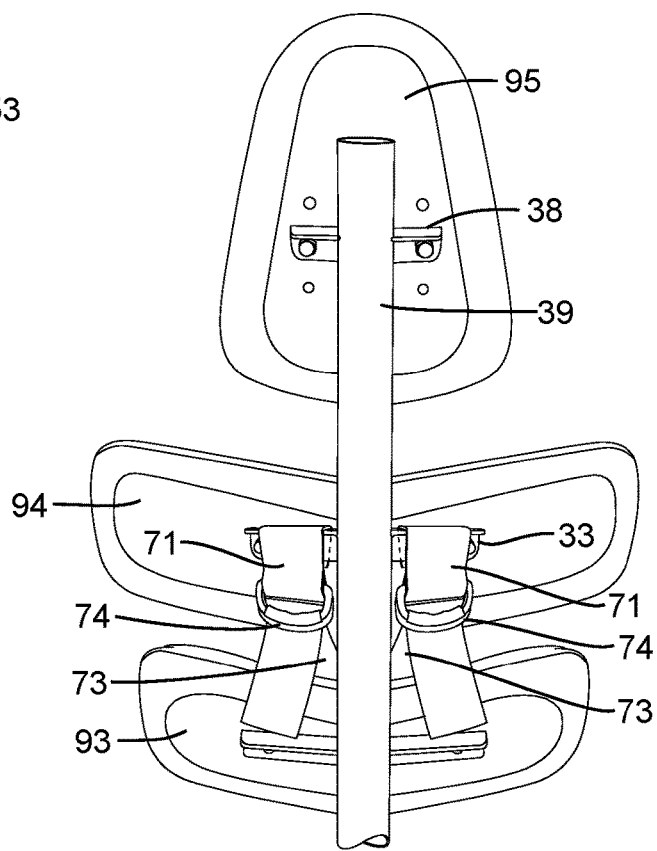
FIG. 8 is a rear view of the invention showing the seat backs and the strap anchors and the top straps of the upper body strap and its ability to be adjusted through the "D" rings to accommodate different size users.
Figure 9:
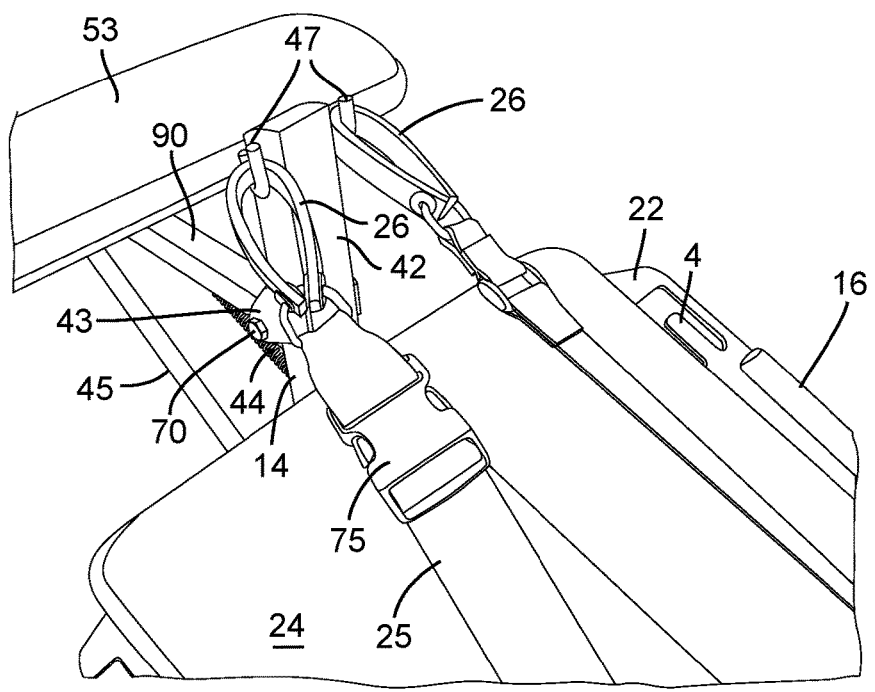
FIG. 9 is a downward view of the seat bottom, lower strap with elastomers looped over anchor points and anchor point support tube shown in the upright position and the leg rest shown in the upright position.

In FIG. 7, latch mechanism 59 is pivotally attached to tube 14 by pivot bolt 72 and is configured to engage latch pin 79 to keep the foot rest from rising and the seat back from reclining before the individual is outfitted with torso strap 27 and lower strap 25.

Figure 6:
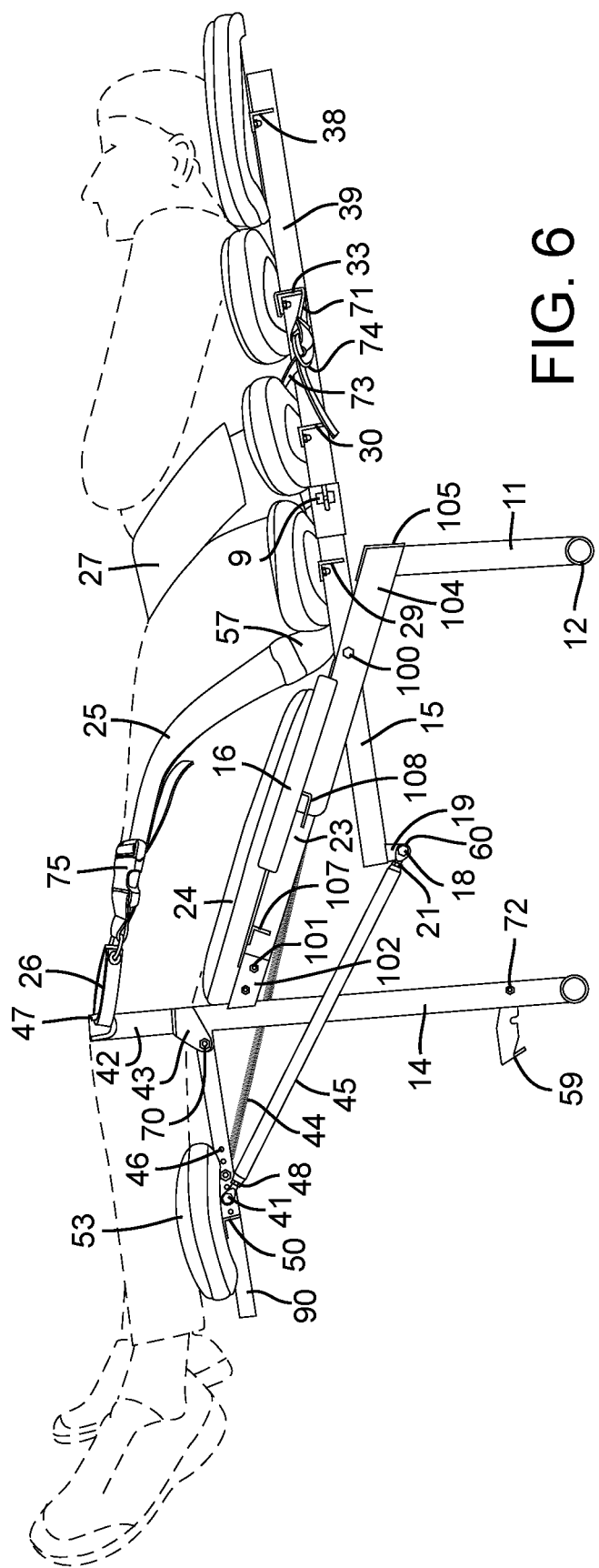
FIG. 6 is a left side view of the present invention in the reclined position with an individual shown in dotted lines.
Figure 6A:
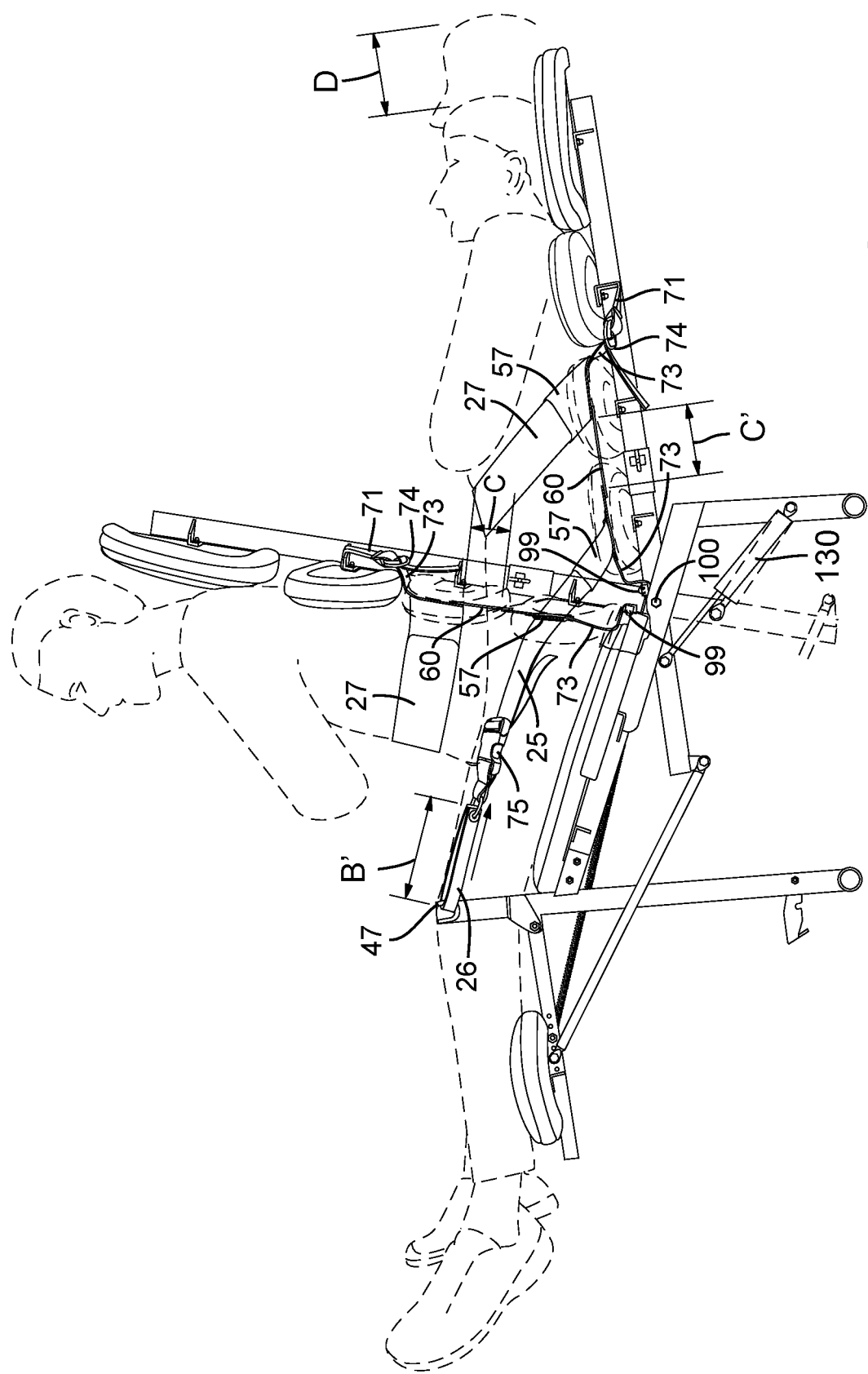
FIG. 6A is a left side view of the present invention in both the upright and reclined position with an individual shown in dotted lines.

In FIGS. 3 and 6, tube 42 is pivotally is welded to plate 43 which is pivotally attached by means of through bolt 70. Bracket 50 is welded to tube 90. Pan 51 is attached to bracket 50 by means of a cap screw and nut 52. A series of holes 46 are strategically placed in tube 90 for the purpose of engaging the end of rod 45 by means of rod end 48 and pivot bolt 41. Rod end 48 and pivot bolt 41 are configured to permit rotation of rod 45 about holes 46. The opposite end of rod 45 is fitted with rod end 21. Through bolt 18 is connected to plate 19. The above combination of tube 90, rod 45 and plate 19 which is attached to the lower end of tube 15, when the invention is put to use by an individual, permit the controlled reclining of backrest support tube 39 while leg support pad 53 elevates with the individual's legs and the individual moves from a seated position to a supine position, FIG. 12.

In FIG. 6, it will be appreciated that the location of Rod ends 21 and 48 located at opposite ends of rod 45 can be placed in different locations in tube 90 enabling the present invention to be adjusted to accommodate individuals with different body characteristics. An individual with heavy upper body and light legs may require an adjustment that is different than an individual with light upper body and heavy legs. This adjustment is possible by selecting the correct location of pivot points for rod end 48 in the correct holes in tube 90.

Figure 4:
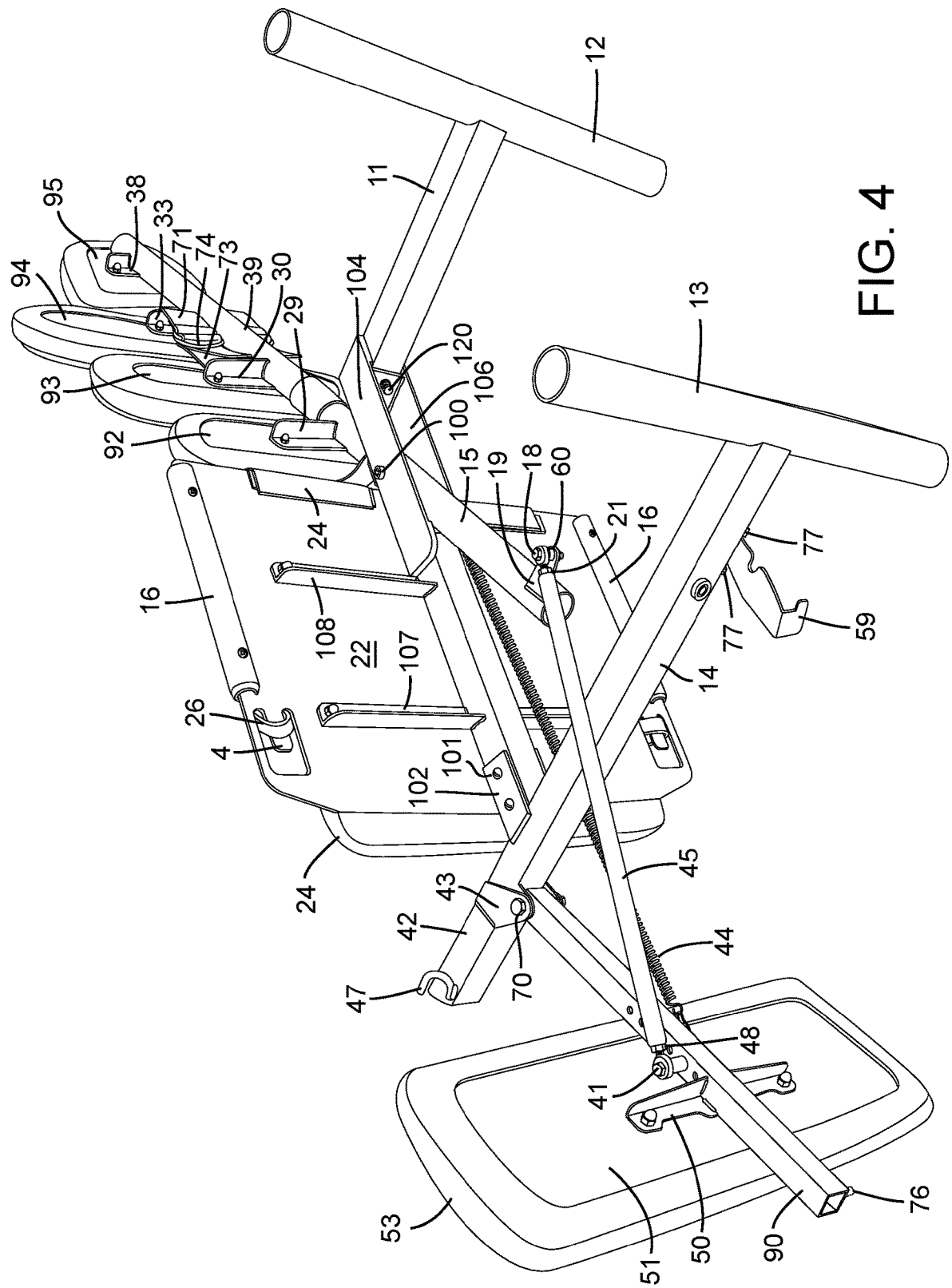
FIG. 4 is a pictorial view of the present invention in the reclined position from beneath and to the right.

In FIG. 3, spring 44 is attached to tube 90 and while the invention is in the upright position, spring 44 is in the non-stretched position. In FIG. 4, spring 44 is shown in the stretched position because the invention is shown in the reclined position. It will be appreciated that tube 90 has a series of holes 46, where spring 44 may be attached allowing the return pull force to be adjusted by means of moving the attachment point from one hole to another. More return pressure is possible with the spring attached to the lower holes or the holes at a greater distance from the pivot point 70. The opposite end of spring 44 is attached to plate 106 and pivot bolt 100, hidden from view in the respective figures.

The seat pan 22 and seat back pans 92, 93, 94 and 95 all have padded cushions attached to provide comfort to the individual when using the present invention. It will also be appreciated that lower body strap 25 is configured to slide back and forth through enclosing material 57 and wrap around the buttocks at the hips forward from the sacral area of the spine traversing around each side of the hips forwardly and over each thigh to be anchored by elastomers 26 at anchor points 47. It will be further appreciated that this routing of the lower body strap, effectively grasping the hips and buttocks is much more effective than the lower body strap presently available in the flat traction table mentioned above. This means of securing the hips and buttocks does not permit slipping of the lower strap or encourage sliding of the pants of the user relative to the user's body. As the user reclines, the buttocks is pulled rearward following the upper body as it is pulled rearward by strap 27 but the lower body strap 25 prohibits movement of the buttocks except to the extent that elastomers, pair 26 allow. Elastomers 26 may be made of differing elasticity resulting in the ability to vary the return force applied to lower body strap 25 thereby applying a tensile force on the lower body applied through the hips and buttocks.

In FIG. 10 it will be appreciated that torso strap 27 and lower body strap 25 are configured to be joined by elastic material 60. It will be further appreciated that elastic material 60 holds lower body strap 25 in proper vertical alignment with the user's body relative to torso strap 27. As the user reclines, torso strap 27 moves away from anchor point 47, FIG. 6. Elastic material 60 is permitted to stretch relative to lower body strap 25. As the user reclines, torso strap 27 pulls the user's body away from anchor points 47. As the user's body is pulled away from anchor points 47, lower body strap 25 maintains its grasp on the user's lower body and begins to follow the user's body away from anchor points 47. As lower body strap 25 moves away from anchor points 47, elastomers 26 are stretched and begin to pull the user's lower body back toward anchor points 47 resulting in stretching of the lower back and spinal column.

Figure 1:
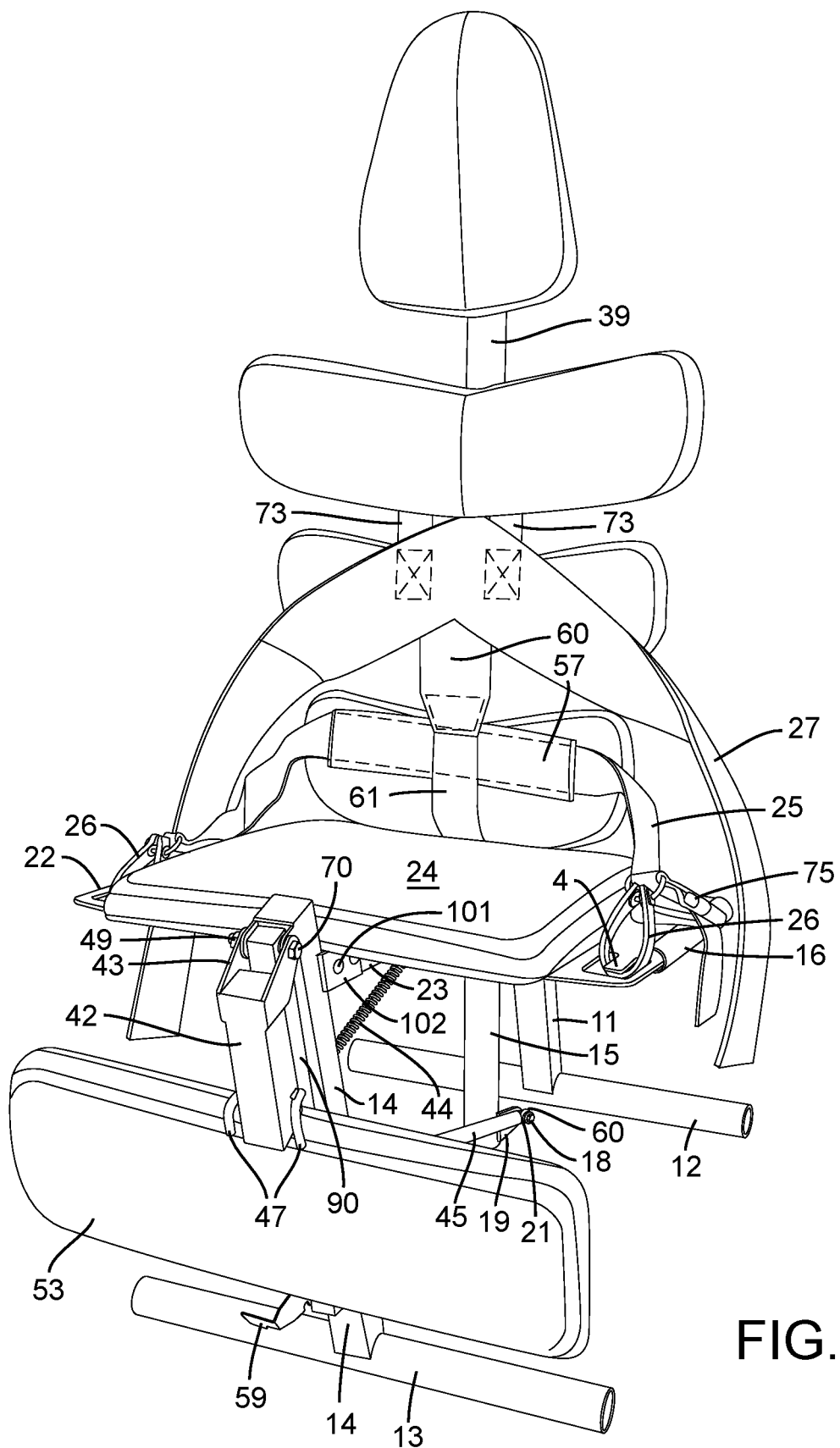
FIG. 1 is a pictorial view of the present invention in the upright position.
Figure 2:
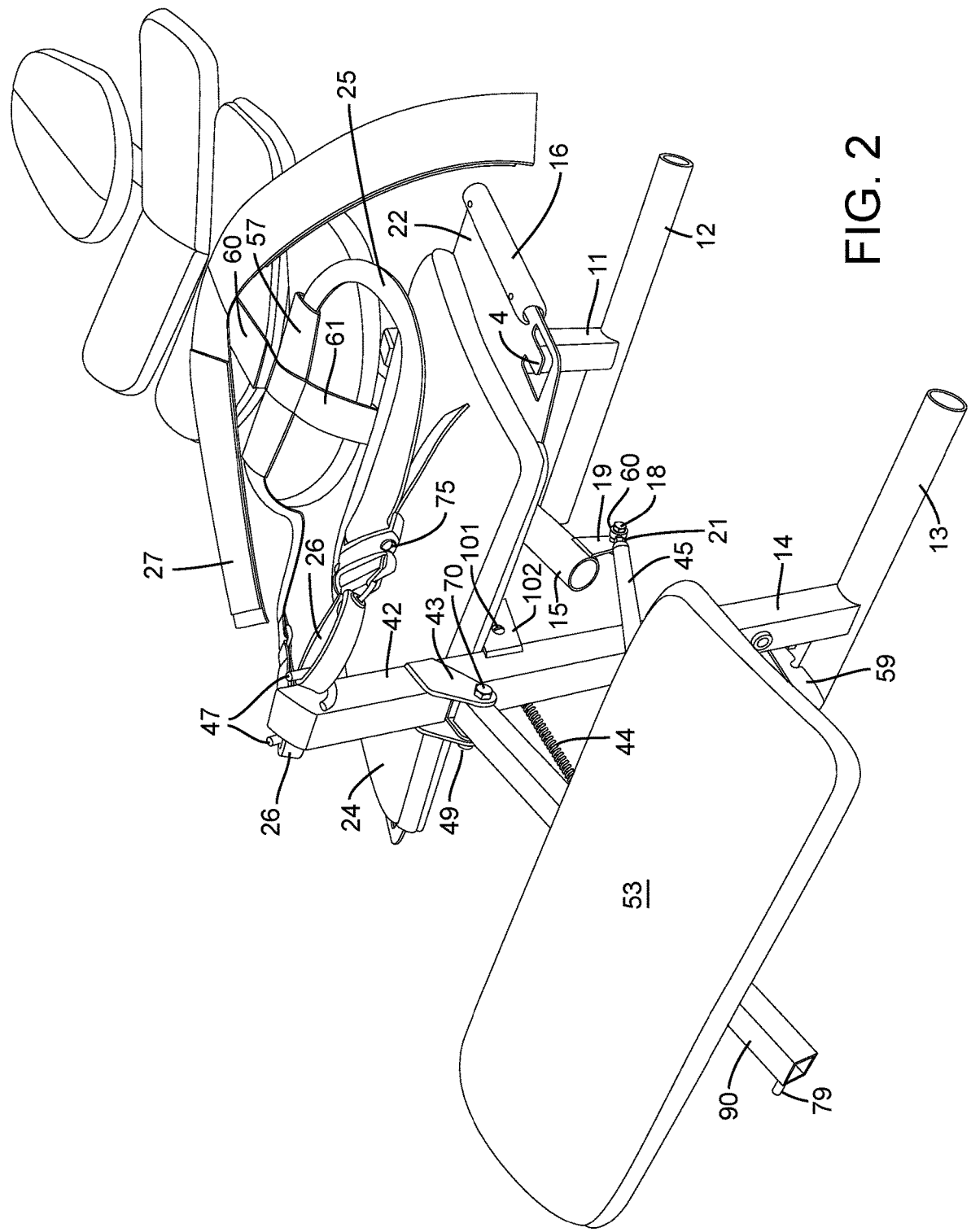
FIG. 2 is a pictorial view of the present invention in the reclined position.

In FIG. 6 it will be appreciated that anchor point support post 42 is in the up position. In FIG. 1, anchor point support post 42 is in the down position. Anchor point support post 42 is configured to pivot about pivot 70 to permit easy seating and standing and stepping away from the present invention. Pivot 70 permits anchor post 42 to rotate downward and away from seat 24 making seating easier.

It will further be appreciated that the upper torso is held by adjustable strap 27 which may be securely wrapped around the lower abdomen just below the ribcage. Strap 27 may be adjusted upward or downward relative to seat back bracket 33 to accommodate different size users. After successful adjustment, torso strap 27 may be tightened comfortably and securely about the waist of the user just below the ribcage. It will be further appreciated that the combination of lower body strap 25, elastomers 26 and upper body strap 27 grasp the user's lower body and upper body slightly above and slightly below the waist and gently pull the user's upper body away from the user's lower body providing a gentle stretching of the lower back and spinal column resulting in the application of traction to the lower back and providing spinal decompression.

Figure 15:
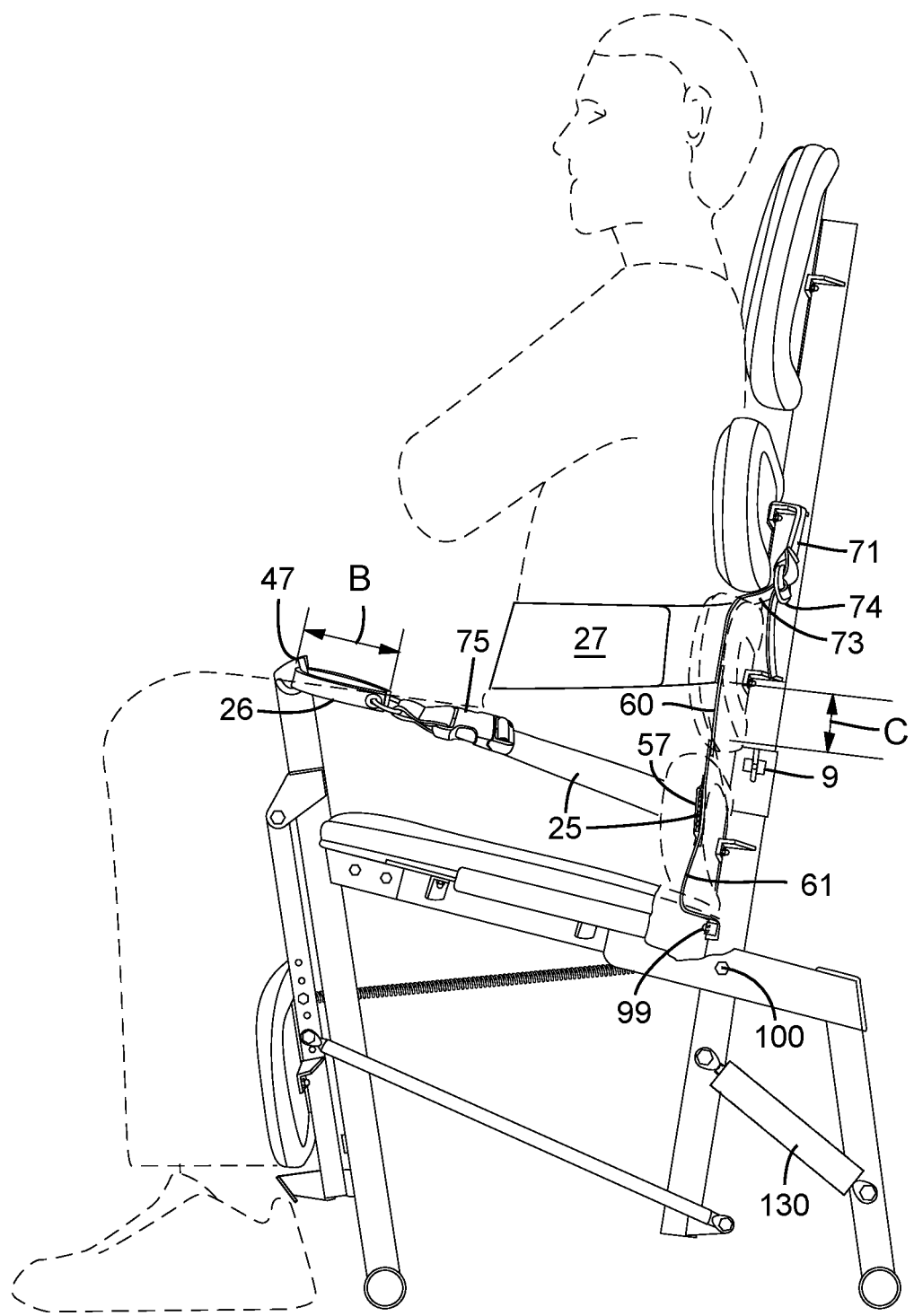
FIG. 15 shows a side view of the invention in the upright position with hydraulic actuator between the vertical support and the seat back tube in the collapsed on non-extended position.
Figure 16:
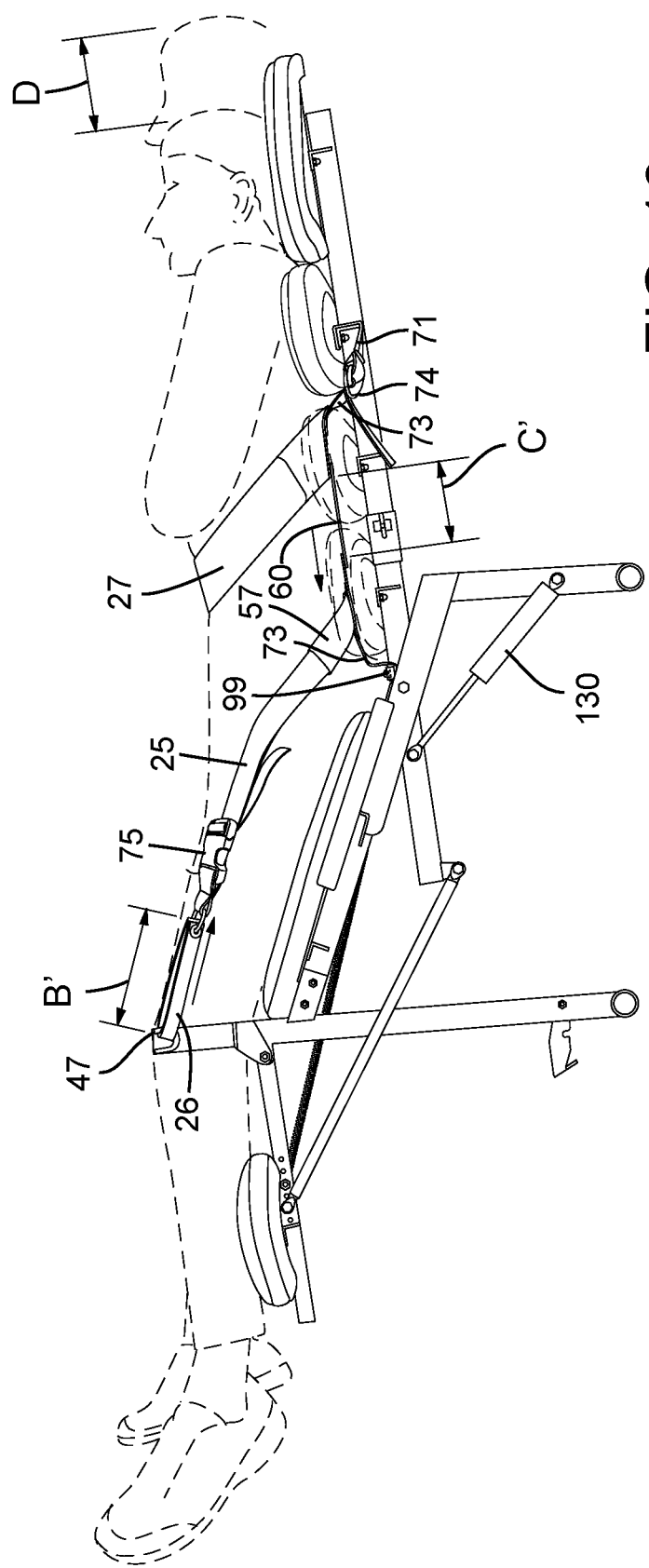
FIG. 16 shows a side view of the present invention in the reclined position with the hydraulic actuator between the vertical support and the seat back tube in the extended position.

In FIGS. 15 and 16 hydraulic actuator 130 is shown in the non-extended position in FIG. 15 and the extended position in FIG. 16. It will be appreciated that by extending or collapsing hydraulic actuator 130, the present invention may be controlled by remote control administered by a doctor or therapist.

In FIGS. 15 and 16 bottom end of torso strap 27, designated in this part of strap assembly 27 as 61, is shown behind dotted lines attaching to tube 15 by means of screw and flat washer 99. Screw and flat washer 99 keep upper and lower strap assemblies 25 and 27 in proper orientation when the invention is not occupied by an individual and allow strap 25 and strap 27 to be located properly relative the user's body when the user sits down and places lower strap 25 around the hips, over the thighs and attached to anchor point 47 by means of elastomers 26. Then torso strap 27 wraps around the upper body under the ribcage.

The assembly of the lower and upper body strap can be best appreciated by studying FIGS. 1, 2, 4, 8, 9, 10, 11, 12, 13, 14, 15 and 16. In FIGS. 1, 4 and others, straps 73 are shown sewn to upper body strap 27 near the top of the apex of the strap. The two straps 71 are clamped between seat back bracket 33 and seat back pan 94. "D" rings 74 are sewn to ends of straps 71 and the tops of back rest straps 73 are woven through "D" rings 74 to permit adjustment of upper body strap 27 by means of straps 73 to accommodate different sized upper torsos. In the preferred embodiment, strap 27 has a male and female Velcro section at the distal ends of the strap. This allows for the strap 27 to overlap and thereby be adjustable for individuals with different waist sizes. Sewn to the bottom of strap 27 just beneath the apex of the two lateral sections is elastic material 60. Elastic material 60 permits the lower strap 25 to be held in the proper relation to the sacral area of the user's lower back and also stretch to permit the upper body strap 27 to move away from lower body strap 25 when the user reclines from a seated to a supine position. Strap 61, FIG. 10, is sewn to the bottom of elastic material 60 and continues toward the bottom of seat back tube 15. In FIGS. 10 and 11, an envelope of material 57 is sewn around lower strap 25 and 57 is in turn sewn to strap assembly 73 and 61. Envelope 57 permits strap 25 to slide through envelope 57 permitting strap 25 to be adjusted. Strap 25 is adjustable to permit the amount of pull on the lower body to be adjusted to suit the amount of spinal decompression or the amount of traction force applied to the lower back of the user. As strap 25 is progressively tightened, loops 26 stretch progressively further as the user reclines and his or her body is pulled away from anchor points 47 causing stretched loops 26 to pull the lower body back towards the anchor points 47 progressively harder and therefore create a greater amount of movement of the spinal column, greater decompression and more stretching of the lower back. Strap assembly 61, non-stretchable, now continues downward as a single strap and attaches to lower seat back tube 15 at screw and washer 99. Anchor point 99 keeps the upper and lower body straps in approximately the correct position relative to the user's body.

Figure 14:
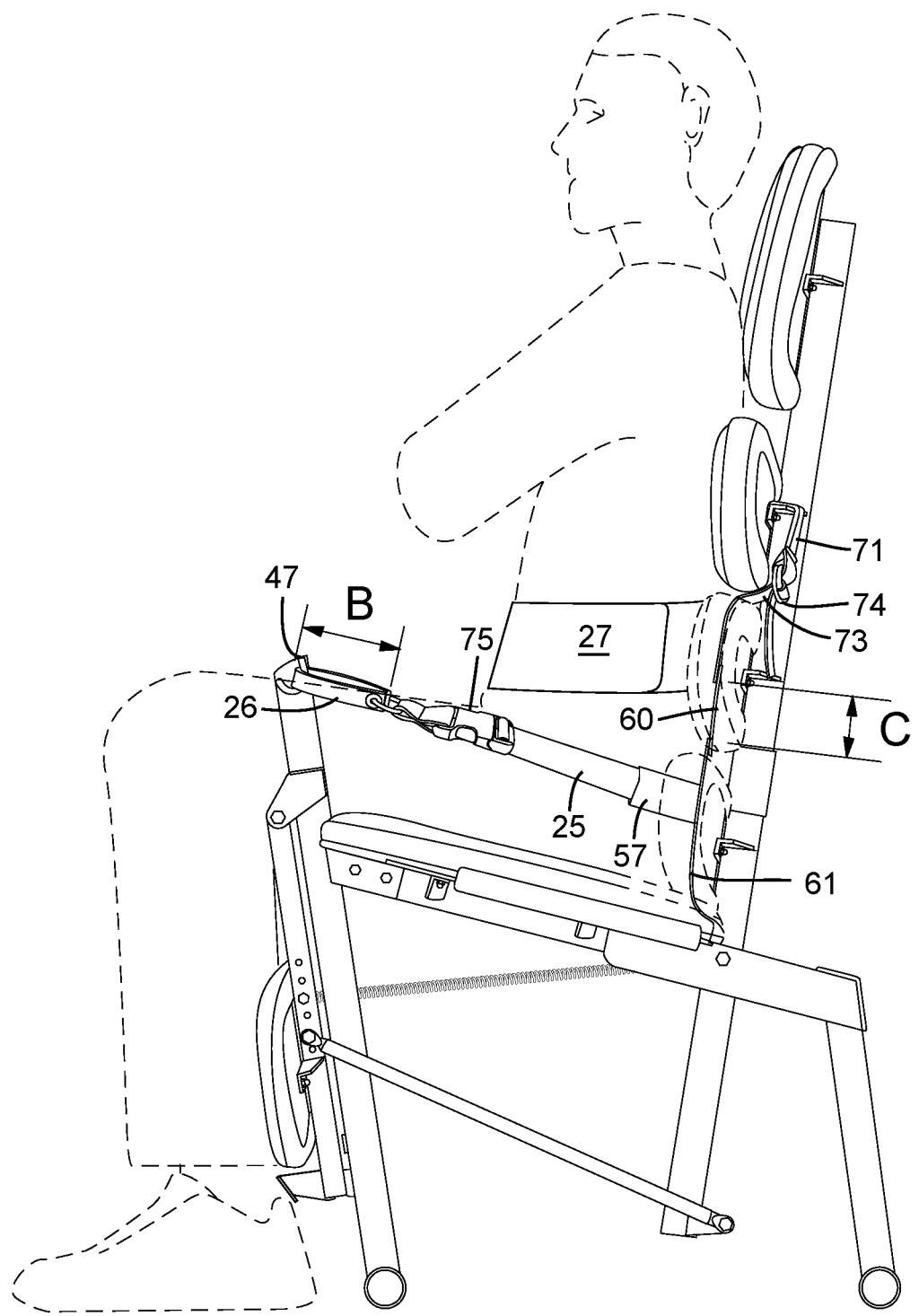
FIG. 14 shows a side view of the present invention indicating the ability of elastomers to stretch at "A" and "C.

As the user reclines, loops 26 and elastic material 60 stretch in length from "B" to "B'" and from "C" to "C'" respectively, in FIGS. 14 and 13.

It will be appreciated that elastic material 60 is sufficiently strong to hold lower body strap 25 at the sacral area of the user's lower back. Elastic material 60 stretches as the user reclines permitting upper body strap 27 to move away from lower body strap 25.

Although in the preferred embodiment the upper body strap is secured about the individual just below the ribcage this is not meant to be a limitation of the present invention. Any location of the upper body strap which enables the present invention to comfortably grasp the user's upper body is considered to be part of the present invention.

In the preferred embodiment the upper and lower body strap assembly is very important. The upper body strap is designed to drop downward as it circles the user's upper body just under the ribs and encloses the torso in the front of the user by means of the Velcro strap sections. Likewise the lower strap is designed to wrap around lower body beginning at the rear of the user's back at the sacral area around the hips and over the thighs and forward to the securing points at anchors 47. This path of the lower strap 25 effectively grasps the user's lower body in a manner that is comfortable, does not slip and helps maintain a correct arch to the lower back.

Mike Lofgren
Sean Harrington
Brian Stewart

The invention claimed is:

1. A method for treating back pain comprising:
    (a) providing a back traction device having at least a frame, a seat bottom attached to the frame, a seat back, a first harness, a second harness and a leg support;
    (b) positioning a person on the back traction device by fastening the person's upper body with the first harness to the seat back and fastening the person's lower body with the second harness to the seat bottom;
    (c) Reclining the seat back thereby causing
        (1) the seat back to recline rearwardly while moving away from the seat bottom;
        (2) the leg support to rotate upwardly supporting the person's legs; and,
        (3) the person's upper body to move away from the person's lower body causing traction of the person's lower back.

2. The method of claim 1 providing a locking mechanism.

3. The method of claim 2 where the person sits in the chair, fastens the harness to their upper body;
    fastens the harness to their lower body;
    reclines back whereby the upper harness moves away from the lower harness providing a stretching of the lower back.

4. The method of claim 3 where the person sits in the chair, fastens the harness to their upper body;
    Fastens the harness to their lower body;
    Releases the locking mechanism;
    reclines back whereby the upper harness moves away from the lower harness providing stretching of the lower back.

5. The method of 2 whereby the locking mechanism prevents inadvertent recline of the seat back.

6. The method of 1 whereby the person experiences stretching of the lower back.

7. A method for treating back pain comprising:
    (d) providing having at least a frame, a seat back and a seat bottom attached to the frame
    (e) fastening the person's upper body to the seat back
    (f) fastening the person's lower body to the seat bottom
    (g) reclining the seat back wherein said reclining results into
        (1) cause the seat back to recline rearwardly thereby, move away from the seat bottom
        (2) cause the fastening of the upper body to pull the person's upper body back as the seat back reclines.
        (3) causing traction of the person's the lower back.

8. The method of claim 7 where fastening is by a harness.

9. The method of claim 8 providing a locking mechanism.

10. The method of 9 whereby the locking mechanism prevents inadvertent recline of the seat back.

11. The method of claim 7 providing a locking mechanism.

12. The method of claim 11 where the person sits in the chair, fastens their upper body;
fastens their lower body;
reclines back whereby their upper body moves away from their lower body providing a stretching of the lower back.

13. The method of claim 12 where the person sits in the chair, fastens their upper body;
Fastens lower body;
Releases the locking mechanism;
reclines back whereby their upper body moves away from their lower body providing stretching of the lower back.

14. The method of 11 whereby the locking mechanism prevents inadvertent recline of the seat back.

15. The method of 7 whereby the person experiences stretching of the lower back.

16. A method for correcting lower back posture comprising:
(a) providing at least a frame
(b) providing a seat attached to the frame for seating a person
(c) providing a post attached to the frame
(d) providing fastening of the person's buttocks to the post
(e) providing tightening between fastening of the person's buttocks and the post
 1. cause grasping of the person's lower back whereby said tightening will pull the person's lower back forward toward the post causing a correction of the posture of the lower back of the person.

17. The method of claim 16 where fastening is by a harness.

\* \* \* \* \*